United States Patent [19]
Maget

[11] Patent Number: 5,788,682
[45] Date of Patent: Aug. 4, 1998

[54] APPARATUS AND METHOD FOR CONTROLLING OXYGEN CONCENTRATION IN THE VICINITY OF A WOUND

[76] Inventor: Henri J.R. Maget, 6455 La Jolla Blvd., La Jolla, Calif. 92037

[21] Appl. No.: 430,504

[22] Filed: Apr. 28, 1995

[51] Int. Cl.$^6$ .................................................. A61M 35/00
[52] U.S. Cl. ............................. 604/290; 604/304; 607/50
[58] Field of Search ................................. 604/23–25, 20, 604/304, 305, 307, 290; 128/202.12, 202.26, 747; 600/21, 22; 602/14; 607/50

[56] References Cited

U.S. PATENT DOCUMENTS

| | | |
|---|---|---|
| 3,489,670 | 1/1970 | Maget . |
| 4,224,941 | 9/1980 | Stivala . |
| 4,328,799 | 5/1982 | LoPiano . |
| 4,402,817 | 9/1983 | Maget . |
| 4,407,282 | 10/1983 | Swartz . |
| 4,522,698 | 6/1985 | Maget . |
| 4,539,086 | 9/1985 | Fujita et al. . |
| 4,608,041 | 8/1986 | Nielsen . |
| 4,640,689 | 2/1987 | Sibalis . |
| 4,648,955 | 3/1987 | Maget . |
| 4,687,423 | 8/1987 | Maget et al. . |
| 4,752,285 | 6/1988 | Petelenz et al. . |
| 4,808,152 | 2/1989 | Sibalis . |
| 4,886,514 | 12/1989 | Maget . |
| 4,902,278 | 2/1990 | Maget et al. . |
| 5,578,022 | 11/1996 | Scherson et al. ................ 604/303 |

FOREIGN PATENT DOCUMENTS

| | | |
|---|---|---|
| 2656218 | 6/1991 | France . |
| 8301388 | 4/1983 | WIPO . |
| 9421323 | 9/1994 | WIPO . |

OTHER PUBLICATIONS

"An Electrochemical Oxygen Separator Using an Ion–Exchange Membrane as the Electrolyte," Yuko Fujita et al., Journal of Applied Electrochemistry 16 (1986) 935–940.

"Disposable, Ambulatory Oxygen Supply Technology for Wound Care," Henri J.R. Maget, Presented at the Innovative Wound Care Technologies Conference, Oct. 12, 1990, San Francisco, CA.

*Primary Examiner*—Mark Bockelman
*Attorney, Agent, or Firm*—Brown, Martin, Haller & McClain, LLP

[57] ABSTRACT

A device is described for promotion of human or animal wound healing by controlling oxygen concentration in the environment around the wound. It is light weight, portable, convenient and comfortably worn by the patient. It can operate continuously or intermittently and can patient-controllable or automatic. Its comfort, portability and effectiveness insure that it will be readily used by patients to enhance recovery from skin trauma. The device is a generally flat unit which includes components for electrochemical production of an ionic species at one electrode, transported of the ionic species across an ion permeable membrane, and reaction of the ionic species at a second electrode to be converted to a molecule which results in a net change of concentration of oxygen adjacent to the wound. Medication may also be applied to the wound within the enclosure. The electrical system can powered by an easily replaceable battery. The patient contact portion of the device unit in normally discarded after a single use, and the electrical and membrane components, contained in their own housing, are reused. A method of enhancing wound healing by controlling the concentration of oxygen in the vicinity of a wound using the device is also described.

47 Claims, 4 Drawing Sheets

APPARATUS AND METHOD FOR CONTROLLING OXYGEN CONCENTRATION IN THE VICINITY OF A WOUND

BACKGROUND OF THE INVENTION

1. Field of the Invention

The invention herein relates to promoting healing of wounds to and through the skin of humans or animals. More particularly it relates to promoting such healing by creating an environment surrounding the wound which promotes healing of the damaged tissue.

2. Description of the Prior Art

It is known that providing a supply of oxygen to a wound to or through the skin (e.g., ulcers, abrasions, cuts, sores, etc.) promotes healing of the wound. However, there are no convenient means of providing such an oxygen supply to a wound or regulating the oxygen concentration in the vicinity of the wound. The patient can be placed in some sort of gas-tight enclosure, such as a hyperbaric chamber, but such is extremely expensive and therefore likely to be used only in the most acute cases and then only during the most critical early healing period. A device for treating sacral wounds has been described in by LoPiano in U.S. Pat. No. 4,328,799, with gaseous oxygen being flowed from a stationary supply tank into the interior of the device through tubing. LoPiano's device is designed only for use only by a recumbent, disrobed patient confined to a hospital bed, and must be secured to a rail of the bed. One can envision a similar sleeve-like device cuffed at the ends to surround the area of a wound to a limb, but such a device would be still be stationary, cumbersome and difficult to use. As with the chamber, LoPiano's device and similar devices keep the patient restricted to a single location. Consequently, for patients who are not otherwise confined to a bed, the lack of portability and inconvenience mean that LoPiano devices and the like are used only intermittently (such as when the patient is asleep), if at all, and therefore the effect of the oxygen therapy on the wound is minimal.

Devices utilizing transmission of gases in ionic form through ionspecific membranes have been described previously. I have a number of patents related to such devices, the most relevant of which for the purpose of this invention are U.S. Pat. Nos. 4,402,817 (1983) and 4,522,698 (1985). Oxygen separation using membranes is described in my U.S. Pat. No. 3,489,670 (1970) and by Fujita et al. in U.S. Pat. No. 4,539,086 and *J. App. Electrochem.*, 16: 935–940 (1986). None of the devices or methods described in those references suggests delivery of oxygen to or from a wound site or any device to accomplish that.

It would therefore be of significant value to have a device which would readily, conveniently and continuously provide oxygen to a wound site and control oxygen concentration in the vicinity of the wound to promote wound healing. Such a device would have to be easily portable, cause the patient little or no inconvenience or discomfort, and be simple to maintain.

SUMMARY OF THE INVENTION

The present invention is such a device. The device of this invention covers a reasonably sized wound area, provides an envelope of concentrated or even substantially pure oxygen around the wound, controls the oxygen concentration within the vicinity of the wound, is portable, and is conveniently and comfortably worn by both ambulatory and non-ambulatory patients. It can operate continuously or can be easily stopped and started by the patient. It is sufficiently simply and inexpensive that it can be used once and then discarded, or can be constructed to be sterilizable and reusable. Its comfort, portability and effectiveness insure that it will be readily and enthusiastically used by patients to speed their recovery from skin trauma.

The device is a generally flat, flexible unit which includes equipment for electrochemical generation of oxygen from air by electrochemically producing an ionic species, normally reduced oxygen or oxidized hydrogen (i.e., a proton) at an electrode in a chamber on one side of an ion exchange membrane, transporting the ionic species across the membrane, and on the opposite side of the membrane converting the ionic species to gaseous oxygen in an oxygen concentration chamber, and then dispersing the concentrated oxygen into an enclosure surrounding the wound, such that the enhanced oxygen environment contacting the wound promotes the healing of the wound. The device is reversible, such that the concentration of oxygen can be decreased in the oxygen chamber by causing the oxygen or oxygen containing molecule to be ionized at the electrode on the oxygen concentration chamber side, the ionized species to be transported across the membrane (in the opposite direction) and the ionic species converted to a molecule at the electrode in the other (non-oxygen concentration) chamber. The device itself is lightweight, fully portable, does not restrict the mobility of the patient, and is self-contained. The electrical system is powered by an easily replaceable battery. The patient contact portion of a unit can be discarded after a single use, and the electrical and membrane components, which are contained in their own housing, can be reused repeatedly. The oxygen transport device can also include components to simultaneously provide medication to the wound.

The device is easily and comfortably adhered to a patient's skin surrounding the wound site. It may be used for human treatment of adults, children and infants, and may also have veterinarian uses for animals.

In one embodiment, the invention is a device for the promotion of healing of a wound to or through the skin of a human or animal by controlling the concentration of oxygen to the wound, which comprises: a first chamber distal from the wound, an oxygen chamber open to the wound, and fluid communication between the chambers; ion transport means disposed between the chambers and in fluid contact with both, the ion transport means comprising a pair of electrodes of opposite polarity with an ion-permeable membrane therebetween, a first electrode of the pair in contact with the first chamber and a second electrode of the pair in contact with the oxygen chamber; an electrical current generator operably connected to the electrodes; and an adhering member adjacent to the oxygen chamber for adhering the device to a patient's skin surrounding the wound with the oxygen chamber open to the wound; whereby operation of the electrical current generator causes one of the electrodes to produce an ionic species in the respective chamber, the ionic species to be transported across the ion permeable membrane, and the ionic species to be reacted at the second electrode to be converted to a molecule which results in a net change of concentration of oxygen in the oxygen concentration chamber and adjacent to the wound.

In another embodiment, the invention involves apparatus for promotion of healing of a wound to or through the skin of a human or animal by providing oxygen to the wound, which comprises: an oxygen permeable sheet having a chamber side and a wound side, each of the sides being bounded by a perimeter area and having sufficient surface area within the perimeter area to cover an area of the wound; adhesive on the perimeter area of the wound side to adhere the oxygen permeable sheet to the skin surrounding the wound; an oxygen impermeable sheet adhered to the chamber side of the oxygen permeable sheet over at least a portion of the perimeter area of the chamber side, the adhered sheets thereby forming a hollow enclosed chamber therebetween; a housing having an external end and a chamber end and an opening therethrough between the ends, the housing abutting the chamber and having means for gas communication between the chamber end and the chamber; means for ion transport disposed within and sealing the opening through the housing, the means for ion transport comprising an ion-permeable membrane having two sides disposed between the chamber end and the external end of the housing; first electrochemical means adjacent one of the sides of the membrane for forming an ionic species, the species thereafter being transported across the membrane; second electrochemical means adjacent the other of the sides of the membrane for converting the ionic species after transport into a molecule which represents a net change of concentration of oxygen in the chamber; and a voltage differential between the first and second electrochemical means for transporting the species formed at the first electrochemical means across the membrane; whereby operation of the electrochemical means and imposition of the voltage differential effects oxygen movement through the gas communication means, the chamber oxygen and the oxygen permeable sheet causing a change in the oxygen concentration in contact with the wound.

The device is preferably separable into two portions each containing one chamber, with the ion transport means and electrical current generator disposed within that portion containing the chamber distal from the wound, such that the two portions may be separated for disposal of the portion containing the chamber adjacent the wound (i.e., the patient contact portion) after each use and reuse of the wound-distal portion with a fresh woundadjacent chamber portion.

In yet another embodiment, the invention involves a method for the promotion of healing of a wound to or through the skin of a human or animal by controlling the concentration of oxygen to the wound, which comprises: forming a first chamber distal from the wound, an oxygen chamber open to the wound, and fluid communication between the chambers; disposing ion transport means between the chambers and in fluid contact with both, the ion transport means comprising a pair of electrodes of opposite polarity with an ion-permeable membrane therebetween, a first electrode of the pair in contact with the first chamber and a second electrode of the pair in contact with the oxygen chamber; providing an electrical current generator operably connected to the electrodes; and providing an adhering member adjacent to the oxygen chamber for adhering the device to a patient's skin surrounding the wound with the oxygen chamber open to the wound; and operating the electrical current generator to cause one of the electrodes to produce an ionic species in the respective chamber, the ionic species to be transported across the ion permeable membrane, and the ionic species to be reacted at the second electrode to be converted to a molecule which results in a net change of concentration of oxygen in the oxygen concentration chamber and adjacent to the wound.

Controlling the concentration of oxygen in the vicinity of the wound may comprise maintaining the concentration at a constant level, increasing the concentration, or decreasing the concentration. An oxygen concentration sensor may be included in the system and the device may be operated in response to the concentration signal from that sensor to maintain or vary the oxygen concentration as desired in either portion of the device.

Electrochemical oxygen transfer reactions which can be utilized in the present invention include:

At the anode: $2H_2O \rightarrow 4H^+ + O_2 + 4e^-$

At the cathode: $O_2 + 4H^+ + 4e^- \rightarrow 2H_2O$ with the net reaction being the depletion of gaseous oxygen ($O_2$) on one side of the membrane and increase of the oxygen concentration on the other side.

Alternatively,

At the anode: $4OH^- \rightarrow 2H_2O + O_2 + 4e^-$

At the cathode: $O_2 + 2H_2O + 4e^- \rightarrow 4OH^-$ with the net reaction again being the depletion of gaseous oxygen ($O_2$) on one side of the membrane and increase of the oxygen concentration on the other side.

Other electrochemical or electrolysis reactions which effect a net change in the oxygen concentration on one side of the membrane but do not involve depletion or reduction of oxygen or require the presence of air include, in an acidic medium At the anode: $2H_2O \rightarrow O_2 + 4H^+ + 4e^-$ At the cathode: $4H^+ + 4e^- \rightarrow 2H_2$ with the net reaction being the transfer of protons across the membrane and the generation of gaseous oxygen ($O_2$) on the downstream side of the membrane.

Alternatively, in an alkaline medium

At the anode: $4OH^- \rightarrow 2H_2O + 4e^- + O_2$

At the cathode: $4H_2O + 4e^- \rightarrow 4OH\_ + 2H_2$ with the net reaction being the transfer of hydroxyl ions across the membrane and the generation of gaseous oxygen ($O_2$) on the downstream side of the membrane.

For a device utilizing ambient air and a wetted membrane, the following reactions are typical:

At the anode: $2H_2O \rightarrow 4H^+ + O_2 + 4e^-$

At the cathode: $O_2(air) + 4H^+ + 4e^- \rightarrow 2H_2O$

It will be recognized that either electrode may be operated as anode or cathode, so that the device can be used either to increase or decrease the concentration of oxygen in the vicinity of the wound. Normally the device will be operated to increase or maintain the oxygen concentration about the wound.

Further, it will be clear to those skilled in the art that other electrolytic process can be used to generate oxygen, such as the reversible decomposition of various metal oxides such as nickel or zinc hydroxides.

DETAILED DESCRIPTION AND PREFERRED EMBODIMENTS

The invention will be best understood by reference to the drawings. The embodiment exemplified utilizes an air source and a moist membrane and effectively results in a net transfer of oxygen from the air into the oxygen chamber to increase the oxygen concentration surrounding the wound. As will be evident, however, the device can be operated with various types of membranes, in acidic or alkaline environments, and/or with the presence of small amounts of water, which permit net oxygen concentration increase or decrease or operation in the absence of air, depending on the particular electrochemistry involved. Sufficient water can be obtained from addition of small amounts (usually no more than a few drops) of water to the membrane, or the membrane itself may have a sufficient water content initially. Should the membrane dry out, it can easily be rewetted with a small amount of water.

Figure 1:
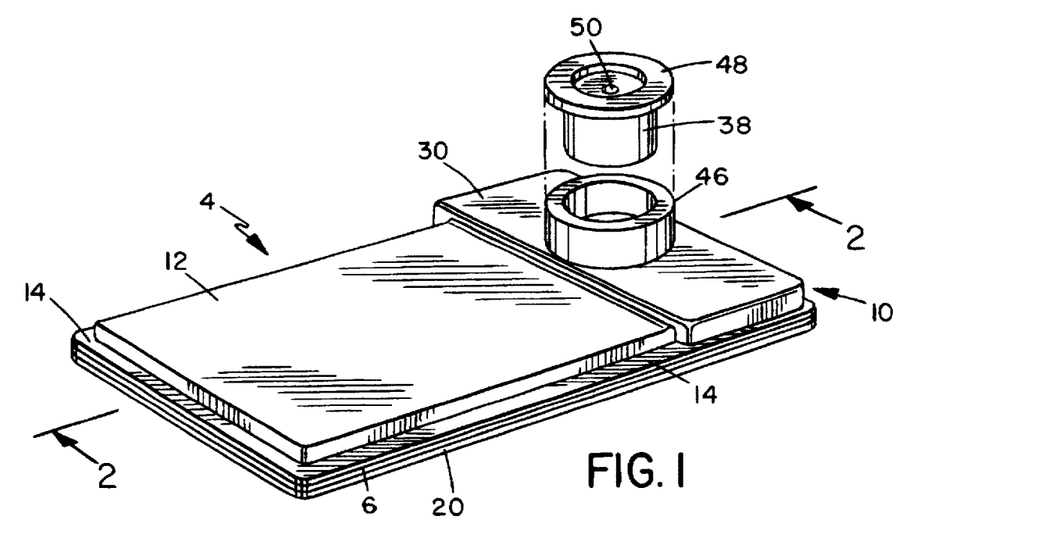
FIG. 1 is a perspective view of one embodiment of the device of this invention.
Figure 2:
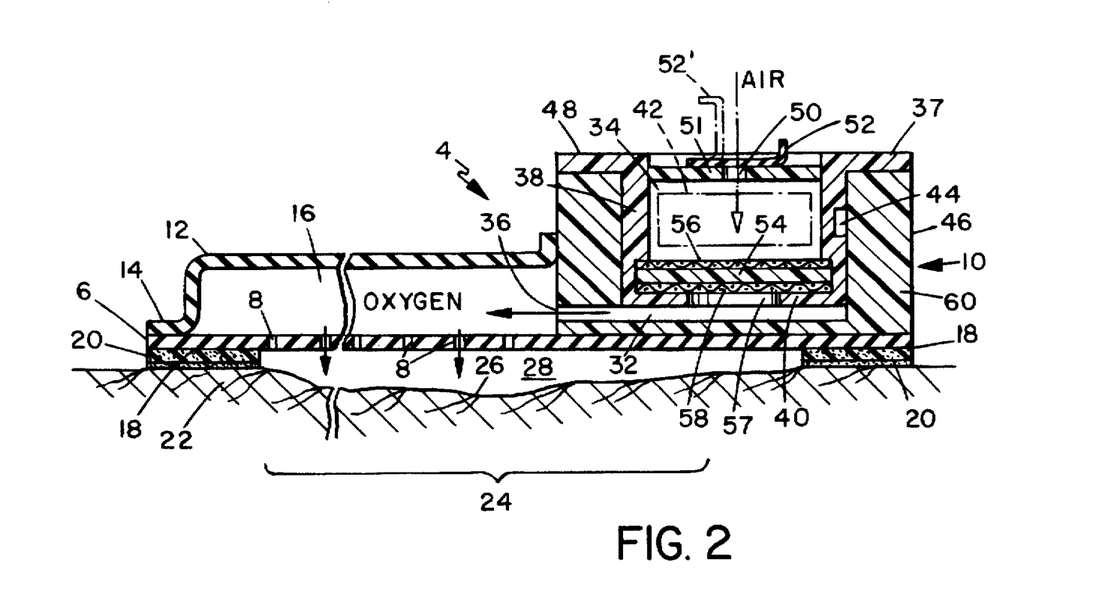
FIG. 2 is a cross-sectional view taken on line 2—2 of FIG. 1, also illustrating the placement of the device over a wound site.

The device 4 as illustrated principally in FIGS. 1 and 2 is in the shape generally of a flattened pad. The base 6 is formed of an sheet material permeable to gaseous oxygen. The base 6 may actually be perforated with formed holes 8, or the sheet material may be a porous membrane whose holes 8 comprise the pores of the membrane, or a non-porous membrane through which oxygen can diffuse. The latter two are preferred, since the device can then be made substantially oxygen-specific by selection of a sheet material which will pass oxygen preferentially, and reduce the passage of other gases, such as nitrogen, argon and carbon dioxide.

At one end of base 6 is the pump section 10, which will be discussed further below.

Attached to the perimeter of the remainder of base 6 is a gas-impervious top sheet 12, which covers the entire expanse of base 6 other than that portion covered by pump section 10. Except at the perimeter 14 top sheet 12 and base 6 are spaced apart, forming a hollow gas chamber 16 between them. Gas chamber 16 has an inlet and its outlet is through the porous or permeable sheet material of base 6 as indicated at 8. Top sheet 12 and base 6 can be joined in any convenient manner, as by an adhesive or by thermal welding, or the entire assemblage of top sheet 12 and base 6 maybe formed as a single molded object from a gas impervious material and then holes 8 formed in the base portion as by mechanical or electrostatic means.

Also attached to the perimeter 14 of base 6, but on the underside 18 thereof, is adhesive strip 20, which completely encircles the base 6. Adhesive strip 20 is used to secure the device 4 to the patient's skin 22 around the wound site 24. The adhesive strip 20 does not touch the wound 26, but serves to cause the base 6 of the device 4 to stand off a slight distance from the wound 26 itself, so that a small volume 28 is formed between the bottom of base 6 and the top of wound 26, which becomes filled with gaseous oxygen emitted from chamber 16 through holes or pores 8 into contact with the wound 26 when the device is in place on a patient's skin 22 and operating. The adhesive strip 20 may be permeable to oxygen gas to prevent undue gas pressure from building up in volume 28, which could harm the patient and would tend to detach the device 4 from the patient's skin. That permeability may be obtained by having formed passageways through the adhesive layer (not shown) but preferably will be obtained by having the adhesive material itself be somewhat porous, since the formed passageways may have a greater tendency to allow contaminants to enter volume 28 when the device is not operating.

The materials of base 6, top sheet 12 and adhesive 20 are all flexible, so that the device can be conformed to the contours of the patient's body surrounding the wound site. However, the device is sufficiently rigid to allow the physician, other medical attendant or the patient to put into place.

The pump section 10 is formed of a material which has some degree of flexibility but is still sufficiently rigid to hold the various operating components and provide for free flow of oxygen through the pump section 10 and into the chamber 16. Pump section 10 is formed of a distribution portion 30 which contains one or more extensions 32 of chamber 16, each of which forms a passage through opening 36 for oxygen to flow from membrane 54 and electrode 58 into the larger portion of chamber 16. The material of pump section 10 is sufficiently rigid to keep extensions 32 open whether or not the device is operating.

An annular member 46 is included in pump section 10 and is closed by removable cap 48, which holds ion-specific membrane 54, electrodes 56 and 58, battery 42 and controller 44, and whose interior forms air chamber 34. Annulus 46 is shown in FIGS. 1 and 2 as being elevated, but annulus 46 and distribution portion 30 may be constructed to be of the same height so that the top of cap 48 is substantially flush with the top of distribution portion 30. Cap 48 has an annular wall 38 with a top flange 37 projecting outwardly and a bottom flange 40 projecting inwardly. A removable plug 51 is fitted into the center of the top of cap 48 and contains an inlet hole 50 for passage of air into chamber 34. Hole 50 can be closed by an impervious flexible flap 52. Annulus 46 will normally be located at the center of pump section 10, but may be offset to one side or the other if desired. Pump section 10, cap 48 and annulus 46 may be made of any convenient gas impervious chemically inert and electrically non-conductive material such as plastic or rubber.

Positioned at the boundary or interface between air chamber 34 and extension 32 of oxygen chamber 16 and extending across the gas flow path between them is permeable membrane 54, which has electrode 56 on its air chamber side and electrode 58 on its oxygen chamber side. At electrode 56 a cathodic reaction occurs to combine the ambient oxygen from the air into a species, such as water or hydroxyl ions, in which it is present as reduced oxygen. The voltage differential created by electrodes 56 and 58 drives the species across the permeable membrane 54, which is specific to passage of that species. At electrode 58 an anodic reaction occurs to convert the species to release the reduced oxygen as gaseous oxygen in release chamber 57, from which the gaseous oxygen flows through passage 32 into chamber 16 and on to the wound site 24.

For the following reaction examples, it will be assumed that electrode 56 is the cathode and electrode 58 is the anode, which would be the typical operating mode. However, it will be recognized that either electrode may be operated as anode or cathode, so that the device can be used either to increase or decrease the concentration of oxygen in the vicinity of the wound.

Typical of electrochemical oxygen transfer reactions which can be utilized in the present invention include:

At the anode:

$$2H_2O \rightarrow 4H^+ + O_2 + 4e^- \quad (1a)$$

At the cathode:

$$O_2 + 4H^+ + 4e^- \rightarrow 2H_2O \quad (1b)$$

with the net reaction being the depletion of gaseous oxygen ($O_2$) on one side of the membrane and increase of the oxygen concentration on the other side.

Alternatively,

At the anode:

$$4OH^- \rightarrow 2H_2O + O_2 + 4e^- \quad (2a)$$

At the cathode:

$$O_2 + 2H_2O + 4e^- \rightarrow 4OH^- \quad (2b)$$

with the net reaction again being the depletion of gaseous oxygen ($O_2$) on one side of the membrane and increase of the oxygen concentration on the other side.

Other electrochemical or electrolysis reactions which effect a net change in the oxygen concentration on one side of the membrane but do not involve depletion or reduction of oxygen or require the presence of air include, in an acidic medium At the anode:

$$2H_2O \rightarrow O_2 + 4H^+ + 4e^- \quad (3a)$$

At the cathode:

$$4H^+ + 4e^- \rightarrow 2H_2 \quad (3b)$$

with the net reaction being the transfer of protons across the membrane and the generation of gaseous oxygen ($O_2$) on the downstream side of the membrane.

Alternatively, in an alkaline medium

At the anode:

$$4OH^- \rightarrow 2H_2O + 4e^- + O_2 \quad (4a)$$

At the cathode:

$$4H_2O + 4e^- \rightarrow 4OH^- + 2H_2 \quad (4b)$$

with the net reaction being the transfer of hydroxyl ions across the membrane and the generation of gaseous oxygen ($O_2$) on the downstream side of the membrane.

For a device utilizing ambient air and a wetted membrane, the following reactions are typical:

At the anode:

$$2H_2O \rightarrow 4H^+ + O_2 + 4e^- \quad (5a)$$

At the cathode:

$$O_2(air) + 4H^+ + 4e^- \rightarrow 2H_2O \quad (5b)$$

The electrodes 56 and 58 can be in the form of a mesh or a thin coating on the opposite surfaces of membrane 54. They can be made of any materials which are electrically conductive and which will (as the cathode) convert gaseous oxygen molecules in chamber 34 to reduced oxygen in the transfer species, provide a voltage gradient across membrane 54 to move the oxygen containing species, and (as the anode) convert the transfer species to release the reduced oxygen for recombination as molecular oxygen. Suitable electrocatalytic electrode materials include platinum, iridium, rhodium, ruthenium and their alloys and oxides, as well as noble metals on carbon or graphite, for an acidic reaction, and silver, nickel or platinum for an alkaline reaction. illustrative electrode materials are described in the aforesaid Fujita et al. references.

The membrane will be preferentially permeable to the specific type of reduced-oxygen-containing species utilized in a particular device. The species may be neutral (such as water) or ionized (such as hydroxyl ion). However, this invention contemplates use of any type of membrane which will preferentially transport all types of reduced-oxygen-containing species usable herein, including those membranes which may be capable of transport of a plurality of such species. The membranes useful herein will normally be composed of a fluorosulfonic or fluorocarboxylic material, preferably a perfluorosulfonic acid or perfluorocarboxylic acid ionomer. Alkaline membranes, transporting hydroxyl ions, may include membranes with functional groups such as hydroxy ($OH^-$), amino ($-NH_2$) and quaternary ammonium ($-CH_2(CH_3)_3N$). Those skilled in the art will also recognize other membrane materials, whether currently existing or to become available in the future, which have the necessary property of preferentially passing species containing reduced oxygen in a form which can be regenerated as gaseous oxygen without the production of undesirable by-products.

The net result of the foregoing is the effective transfer of gaseous oxygen from air chamber 34 into oxygen chamber 16. The removal of oxygen from air chamber 34 results in a decrease of oxygen partial pressure in chamber 34. The removal of oxygen from chamber 34 causes additional ambient air to be drawn into the chamber 34 through hole 50 replenishing the supply of oxygen in chamber 34. Hole 50 is of sufficient size to permit exchange of air so that the oxygen concentration in chamber 34 does not fall to a point where the operation of the device is impaired, at least until it is desired to turn the device off. Conversely, the new inflow of oxygen gaseous into chamber 57 causes an increase of pressure in that chamber, and causes the reconstituted oxygen gas to flow through passage 32 into chamber 16 and out through permeable back 6 into volume 28 where it contacts the wound 26 in the patient's skin 22. Oxygen concentration in chamber 16 and therefore also in the environment around the wound site 24 will be greater than 21% (ambient air oxygen concentration), preferably at least 50%, and more preferably in the range of 85%–99%. The combination of gas pressure and capillary action causes the oxygen gas to penetrate into the surface region of the skin 22 throughout the wound site 28, enhancing the natural healing process. The oxygen also has a sterilizing effect by suppressing anaerobic bacterial infection in the wound site.

Figures 5, 6:
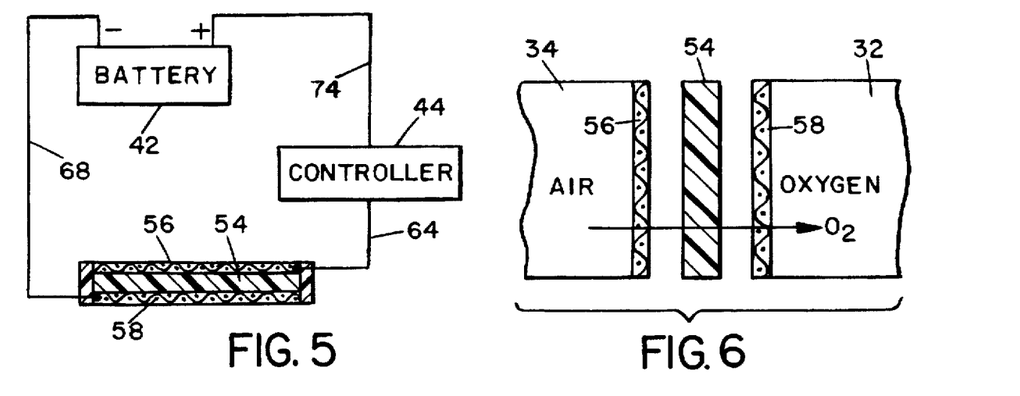
FIG. 5 is a schematic diagram of an electrical circuit for use with the present invention.
FIG. 6 is a schematic diagram illustrating the electrochemical reactions resulting in the net transfer of oxygen across a membrane within the device of the present invention.
Figure 7:
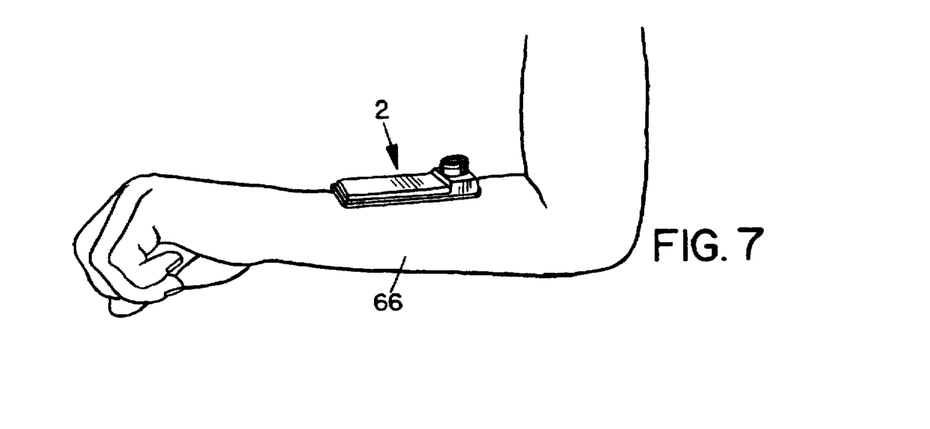
FIG. 7 illustrates a device of this invention in place on a patient's arm.

Membrane 54 and electrodes 56 and 58 are supported in a recess 60 formed in the wall 38 of cap 48, and are supported by flange 40. For ease of construction flange 40 may initially be a separate member attached to the bottom edge of wall 38 after the membrane and electrodes are emplaced. Referring to FIG. 5 along with FIG. 2, it will be seen that conductor 64 is electrically connected to electrode 56 and extends within or on the surface of wall 38 to a controller 44 which is disposed in the air chamber 34 or in the wall 38. A second conductor 68 also passes within or on the surface of wall 38 to connect electrode 58 to battery 42, which is also housed within the air chamber 34. Battery 42 and controller 44 are themselves connected by conductor 74 to complete the circuit. (The circuit may also be formed by connection of electrode 56 to battery 42 and electrode 58 to controller 44.)

Battery 42 may be any small replaceable battery of the type commonly used for powering devices such as hearing aids or watches. The specific battery selected for any particular device of this invention will be dependent upon the rate of oxygen conversion desired and the appropriate physical size of the battery for the size of the device. Access to battery 42 for periodic replacement is gained by removal of plug 51.

The specific embodiment of and presence of controller 44 will depend on the intended use and cost of the device. In a relatively simple embodiment, controller 44 will be replaced by a simple manual off-on switch such as switch 35 from FIG. 3, such that when the switch is on the battery current flows directly through the electrodes. In another embodiment, controller 44 may also be a simple timer operating an off-on switch (which may if desired also be manually operable), so that oxygen generation and transport to the wound are regulated by a predetermined schedule based on the desired flow rate of oxygen to the wound site 24. Alternatively controller 44 can be a wave generator capable of producing intermittent voltage signals of varying duration and repetition rate; switch 35 would also be present so that the device can be turned off when desired. Controller 44 can also be a generator capable of reversing the polarity of electrodes 56 and 58 such that oxygen can be extracted from chamber 16 and released into chamber 34. This action will result in depletion of oxygen over the wound 24, resulting in angiogenesis, the rejuvenation of the microcapillary system within the wound area. Most preferably, however, the controller 44 will include a sensor in the oxygen chamber 16 to measure oxygen pressure in chamber 16. The generation of oxygen will then be regulated to maintain the desired level of oxygen pressure in chamber 16 and the desired quantity of oxygen flowing to the wound site 24.

The controller 44 may be microprocessor based, so that a number of different operational sequences or protocols may be programmed into the device. This provides the physician with the opportunity to tailor the oxygen therapy to the specific needs of each individual patient, particularly ambulatory patients, an ability not available with prior art oxygen therapy devices.

In a least cost, entirely disposable embodiment of the device, the battery 42 is an air-breathing battery, such as a zinc-air battery, and flap 52 is also used to turn the device on or off. If the flap is open in position 52', air moves freely into chamber 34 to reach the battery 42, oxygen is available for transport, and the device operates. If the flap is closed in position 52, makeup air cannot enter the chamber 34 to contact the battery 42, no oxygen is available for transport, and the device stops. The battery 42 will be sealed within the annulus 46 and cap 48 and plug 51 are also sealed. When the battery 42 is exhausted, or the device is removed from the wound site, the device can simply be discarded entirely.

Figure 3:
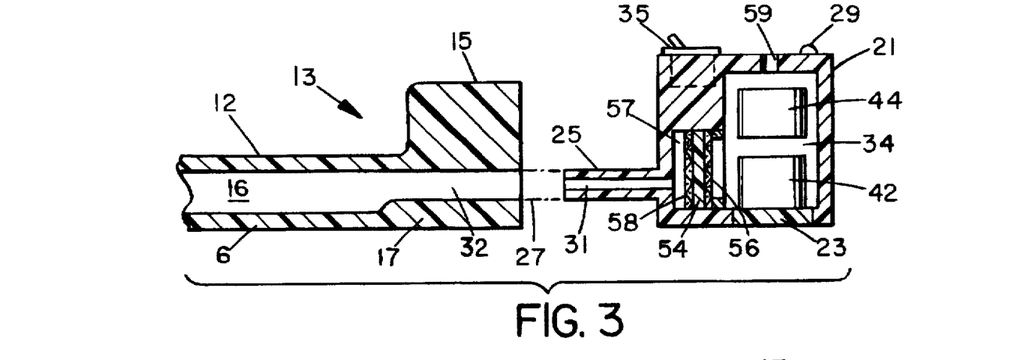
FIG. 3 is a partial cross-sectional elevation view illustrating another embodiment of the invention, and showing how the two principal components fit together.
Figure 4:
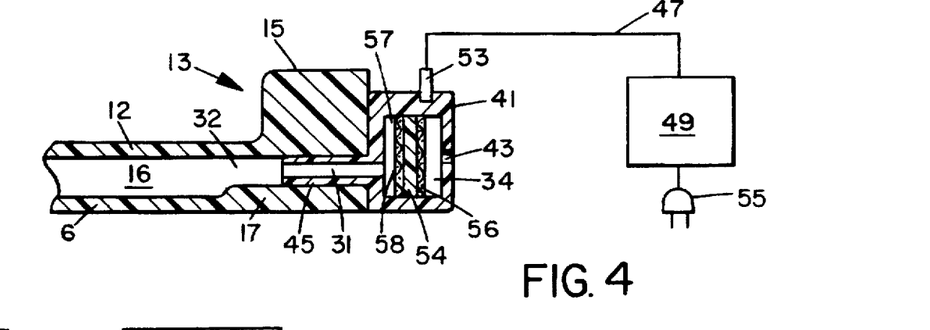
FIG. 4 is a partial cross-sectional elevation view illustrating yet another embodiment of the invention.

Two other embodiments of the device are illustrated in FIGS. 3 and 4, both illustrating a desirable "two-part" structure of many of the embodiments of the device. In FIG. 3 the membrane 54/electrodes 56/58 assembly, the controller 44 and battery 42 are all contained within a removable housing 21, preferably formed of a rigid plastic material. There is an opening 59 in housing 21 to provide air access to the chamber 34, and projection 25 has an axial passage 31 to allow regenerated oxygen gas to flow from chamber 57 into oxygen chamber 16. The housing 21 has an openable panel 23 to provide access to the interior and battery 42, so that the battery can be replaced as needed. Projection 25 is designed to fit into passage 32 in the oxygen chamber portion 13 of the device (as indicated at 27) to secure the housing 21 to the portion 13, as well as serving as an oxygen gas conduit. The fit between the projection 25 and the interior walls of passage 32 will be snug, but still such as to permit relatively easy removal of the housing 21. The end portions 15 and 17 of top sheet 12 and base 6 respectively are thickened and stiffened to cooperate with projection 25 to retain housing 21 and portion 13 together.

Within housing 21 the battery 42, controller 44 and electrodes 56 and 58 are electrically connected together as previously described and illustrated in FIG. 5. Some or all of the conductive wiring may be embedded in the walls of housing 21, with the controller 44 and especially the battery 42 being incorporated into the circuitry by appropriate contacts. A switch 35 may be included in the circuit to turn the device on and off, with an indicator lamp or LED 29 to indicate the status of the circuit.

The embodiment of FIG. 3 lends itself readily to being partially disposable. After use of a device, the housing 21 with all operating component can be removed, the wound-contact portion 13 discarded, and the housing 21 reused with a new portion 13.

Another similar embodiment is shown in FIG. 4, but one in which only the membrane 54 and electrodes 56 and 58 are within the removable housing 41. The projection 45 functions in the same manner as projection 25 of the FIG. 3 embodiment. The housing 41 contains an air access opening 43. The power and control components are housed in the separate unit 49, and are electrically connected to the electrodes through wire 47, which attaches to housing 41 and its internal wiring in any convenient manner, such as by a conventional jack-and-socket connection 53. Unit 49 may be large or small, portable or stationary. It may also contain a converter (not shown) to convert standard AC electricity as from a house circuit to be converted to DC of the appropriate voltage, so that the unit 49 may simply be plugged into house wiring with plug 55 and the house electricity then powering the device 4 and saving drain on batteries. The unit 49 may if desired also include other components, such as a visual display to enable the physician, technician or patient to monitor the operation of the device, an alarm to indicate any malfunction, and so forth. The housings 21 and 41 are preferably interchangeable, so that a patient can use the portable housing 21 when moving around and exchange that for the housing 41 and unit 49 when remaining in one place for a period of time, such as when working at a desk or sleeping. Inclusion of the jack/socket 43 allows the patient to be disconnected from the unit 49 for short periods of time without having to exchange housings 21 and 41. Of course, when unit 49 is disconnected, no oxygen flows into the chamber 16 of the device of FIG. 4.

As noted, the device is sufficiently simple and inexpensive that onetime use and subsequent disposal of the wound contact portion 13 is normally contemplated. Alternatively, however, since usually only the adhesive strip 20 actually touches the skin of the patient (as illustrated in FIG. 5 where the device 4 is shown attached to a patient's arm 66), it is possible that by having replaceable adhesive strips, probably also with the ability to sterilize the wound contact portion 13, the entire device could be reusable for a succession of patients.

The device 4 is contemplated to be constructed in a variety of sizes and shapes to conform to different patient skin areas and different types of wounds. Typically the device will be used for wounds to arms or legs, as illustrated in FIG. 5, and for torso wounds. The device may be square, rectangular, oval, elliptical or round in shape, and will have dimensions appropriate to the type and size of wound to be dressed. Typical sizes for rectangular or square units are 3"–12" (7–30 cm) in each of the length and width dimensions, and up to about 1" (2.5 cm), preferably no more than about 0.5" (1.2 cm), in thickness. The entire device will weigh less than 100 g. The combined thickness of the membrane 54 and the electrodes 56 and 58 will be about 0.1–0.5 mm and each will have a cross-sectional area of about 0.1–10 $cm^2$. The device will deliver about 5–5000 $cm^3$ of oxygen per day. The oxygen pressure in the oxygen compartment can vary depending upon the degree and type of porosity in the base 6, but in most cases the pressure will not exceed about 20–30 mm Hg to prevent vasoconstriction.

Figure 8A:
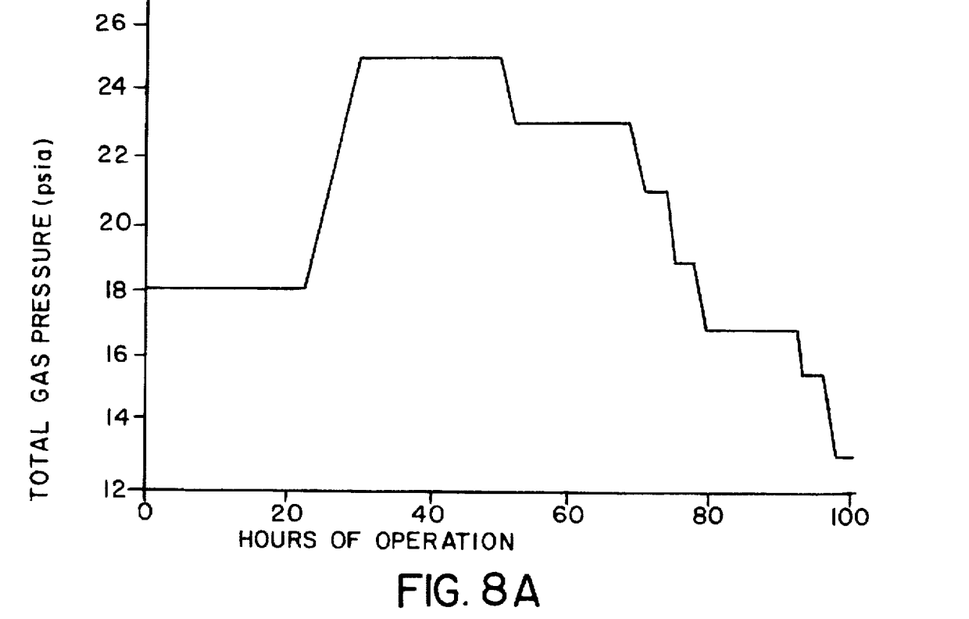
FIGS. 8A and 8B illustrate graphically regulation of total gas pressure generated by control of the current output of a device of this invention.
Figure 8B:
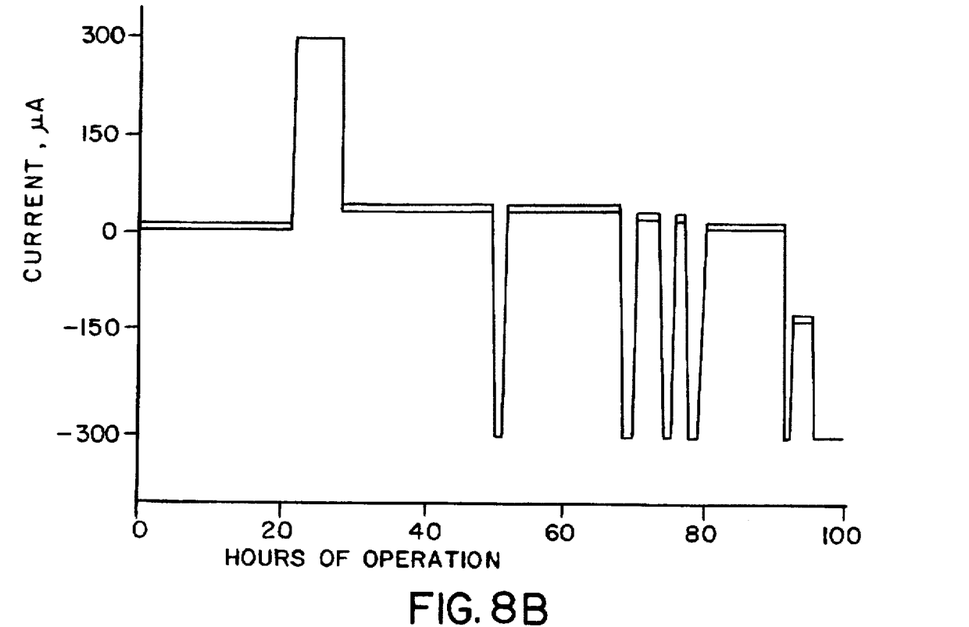
Figure 9A:
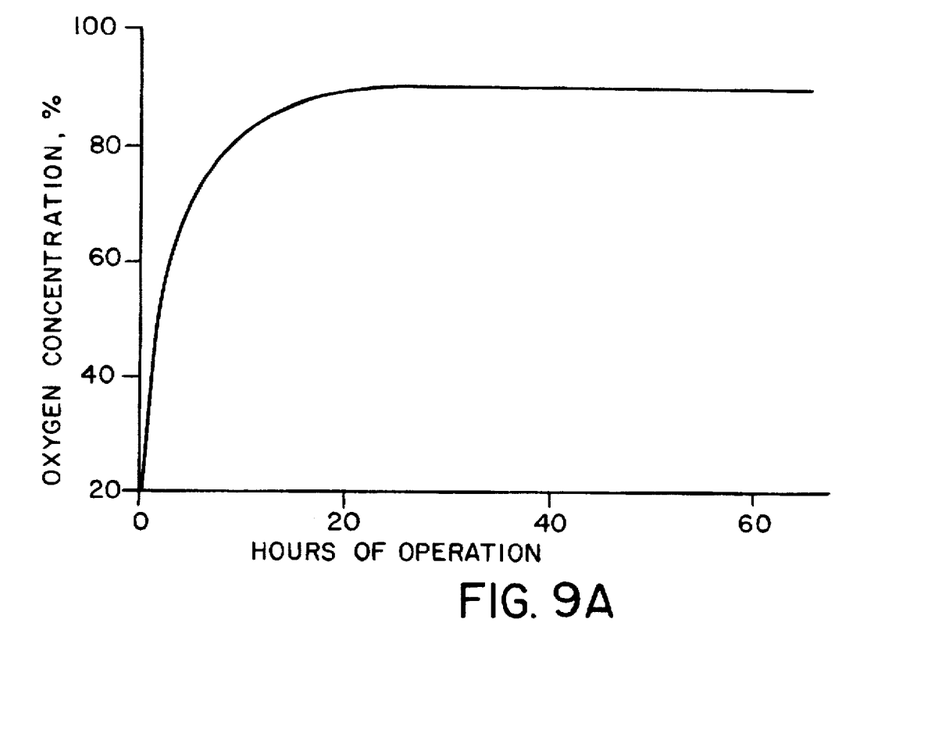
FIGS. 9A and 9B illustrate graphically regulation of oxygen concentration by control of the current output of a device of this invention.
Figure 9B:
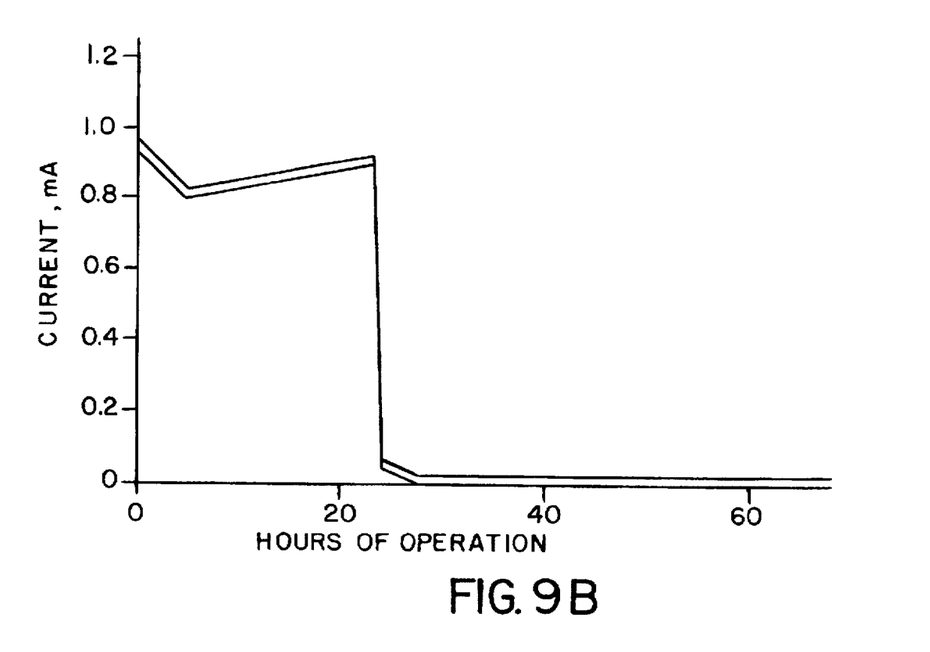

FIGS. 8A and 8B illustrate graphically the regulation of the total gas pressure in the oxygen chamber 16 by control of the electric current through the electrodes 56 and 58. In the device exemplified it will be seen that intermittent current flows of ±300 μA cause the pressure to increase or decrease smoothly over time periods of a few hours. Minute adjustments in current about the baseline of 0 μA (indicated by the crosshatched bars in FIG. 6B) allow the pressure to be readily and continually maintained at desired levels for extended periods of time. Similarly, in FIGS. 9A and 9B, it will be seen that oxygen concentration in oxygen chamber 16 is raised from 21% (ambient air concentration) to 90% over about one day by a continuous current in the range of about 0.8–1.0 mA and then readily maintained by the same type of minute current fluctuations near 0 mA as described for FIG. 8B. Of course, different actual values will be obtained for different size devices designed for various oxygen concentrations and pressure levels. However, the effects illustrated in these Figures will be widely observed.

The device will be useful in promoting and enhancing the healing of numerous types of skin wounds, to both humans and animals. For instance, ulcers, sores, abrasions, cuts, and similar wounds will respond favorably to use of the present device. Since the device is lightweight, comfortable and does not restrict mobility, adults will not object to using it during their everyday activities. It is also anticipated that children and infants can be fitted with the device and will wear it without objection and without trying to remove it. Although the device is relatively unobtrusive, it can be covered with air-permeable light gauze or cloth if desired by a patient. It can also be worn under loose, air-permeable clothing. The device may also have veterinarian uses; because it is comfortable and portable, it may be fitted to any sufficiently large animal, such as a dog or cat, with a skin injury and the animal will be likely to tolerate it.

If desired, the device may also be used in conjunction with means delivering medication to the wound. For instance, the generation of oxygen by the present device would exert gas pressure on liquid or paste medication applied topically to the wound prior to having the device emplaced, thus assisting in dispersing the medication throughout the wound as well as oxygenating the wound. As another possibility, useful for medications which are gaseous and ionizable, cap 48 could be divided axially into two chambers, one for air and the other for a gaseous ionizable medication, each with its own membrane, electrodes and controller, and both powered by battery 42. Oxygen would be transported across one membrane as described herein, while the medication would be transported across the other membrane, and both would be transported to the wound through the extension passages 32 and chamber 16.

It will be evident that there are numerous embodiments of this invention which, while not specifically described herein, are clearly within the scope and spirit of the invention. The above description is therefore intended to be exemplary only, and the actual scope of the invention is to be determined solely by the appended claims.

I claim:

1. A device for the promotion of healing of a wound to or through the skin of a human or animal by controlling the concentration of oxygen at the exposed surface of said wound, which comprises:

a first chamber distal from said wound, an oxygen chamber open to said wound surface, and fluid communication between said chambers;

ion transport means within said device disposed between said chambers and in fluid contact with both, said ion transport means comprising a pair of electrodes of opposite polarity with an ion-permeable membrane therebetween, a first electrode of said pair in contact with said first chamber and a second electrode of said pair in contact with said oxygen chamber;

an electrical current generator operably connected to said electrodes; and an electrically non-conductive adhering member adjacent to said oxygen chamber for adhering said device to a patient's skin surrounding said wound with said oxygen chamber open to said wound;

whereby operation of said electrical current generator causes one of said electrodes to produce an ionic species in the respective chamber, said ionic species to be transported across said ion permeable membrane, and said ionic species to be reacted at said second electrode to be converted to a molecule which results in a net change of concentration of oxygen in said oxygen chamber and adjacent to said exposed surface of said wound.

2. A device as in claim 1 wherein said operation of said one of said electrodes produces an ionic species comprising a proton or a hydroxyl ion.

3. A device as in claim 1 wherein said operation of said one of said electrodes results in the electrolytic formation or dissociation of water.

4. A device as in claim 1 further comprising a controller for controlling the operation of said electrical current generator.

5. A device as in claim 4 wherein said first chamber is closably open to ambient air, said device further comprises a closure to close said air chamber to said ambient air, said electrical current generator comprises an air-breathing battery, and said controller comprises said closure, such that when said closure is closed, said air-breathing battery does not generate electrical current.

6. A device as in claim 4 wherein said controller is an electrical switch.

7. A device as in claim 4 wherein said controller comprises a timer.

8. A device as in claim 4 wherein said controller is microprocessor based and adapted to be programmed for a plurality of operational sequences or protocols.

9. A device as in claim 4 wherein said controller comprises a sensor to determine pressure of oxygen in said oxygen chamber and controls said operation of said electrical current generator in response to said pressure.

10. A device as in claim 9 wherein said in response to said pressure said device operates to increase oxygen concentration in said oxygen chamber.

11. A device as in claim 9 wherein said in response to said pressure said device operates to decrease oxygen concentration in said oxygen chamber.

12. A device as in claim 1 wherein said first electrode operates to form said ionic species and said change of concentration of oxygen in said oxygen concentration chamber comprises an increase in said concentration.

13. A device as in claim 1 wherein said second electrode operates to form said ionic species and said change of concentration of oxygen in said oxygen concentration chamber comprises a decrease in said concentration.

14. A device as in claim 1 wherein said electrical current generator comprises a replaceable battery.

15. A device as in claim 1 wherein said electrical current generator comprises means for converting alternating current to direct current and adjusting the voltage thereof for operation of said electrodes.

16. A device as in claim 1 wherein said oxygen chamber is surrounded by a wall and at least a portion of said wall adjacent to said wound is permeable to gaseous oxygen.

17. A device as in claim 16 wherein permeation comprises apertures formed in said wall.

18. A device as in claim 16 wherein permeation comprises said portion of said wall having pores therethrough.

19. A device as in claim 1 wherein said device is separable into two portions containing respectively said first chamber and said oxygen chamber.

20. A device as in claim 19 wherein said ion transport means and electrical current generator are disposed within that portion containing said first chamber.

21. A device as in claim 19 wherein said portion containing said first chamber is disposed in a housing removably connected to said portion containing said oxygen chamber.

22. A device as in claim 21 wherein said housing further comprises means for providing medication to said wound.

23. A device for the promotion of healing of a wound to or through the skin of a human or animal by providing oxygen at the exposed surface of said wound, which comprises:

an oxygen permeable sheet having a chamber side and a wound side, each of said sides being bounded by a perimeter area and having sufficient surface area within said perimeter area to cover an area of said exposed surface of said wound;

electrically non-conductive adhesive on said perimeter area of said wound side to adhere said oxygen permeable sheet to said skin surrounding said wound;

an oxygen impermeable sheet adhered to said chamber side of said oxygen permeable sheet over at least a portion of said perimeter area of said chamber side, said adhered sheets thereby forming a hollow enclosed chamber therebetween;

a housing having an external end and a chamber end and an opening therethrough between said ends, said housing abutting said chamber and having means for gas communication between said chamber end and said chamber;

means for ion transport within said housing and disposed within and sealing said opening through said housing, said means for ion transport comprising:

an ion-permeable membrane having two sides disposed between said chamber end and said external end of said housing;

first electrochemical means adjacent one of said sides of said membrane for forming an ionic species, said species thereafter being transported across said membrane;

second electrochemical means adjacent the other of said sides of said membrane for converting said ionic species after transport into a molecule which represents a net change of concentration of oxygen in said chamber; and a voltage differential between said first and second electrochemical means for transporting said species formed at said first electrochemical means across said membrane;

whereby operation of said electrochemical means and imposition of said voltage differential effects oxygen movement through said gas communication means, said oxygen chamber and said oxygen permeable sheet causing a change in the oxygen concentration in contact with said exposed surface of said wound.

24. A device as in claim 23 wherein said operation of said first electrochemical means produces an ionic species comprising a proton or a hydroxyl ion.

25. A device as in claim 23 wherein said operation of one of said electrochemical means results in the electrolytic formation or dissociation of water.

26. A device as in claim 23 wherein oxygen permeable sheet contains apertures formed therein.

27. A device as in claim 23 wherein oxygen permeable sheet has pores therethrough.

28. A device as in claim 23 wherein said housing is separable from said chamber.

29. A device as in claim 28 further comprising means for providing medication to said wound in combination.

30. A device as in claim 23 wherein said external end of said housing is closably open to ambient air, said device further comprises a closure to close said external end to said ambient air, said electrical current generator comprises an air-breathing battery, and said controller comprises said closure, such that when said closure is closed, said air-breathing battery does not generate electrical current.

31. A device as in claim 23 wherein said first electrochemical means is disposed on said exterior end said of said membrane and said change of concentration of oxygen in said oxygen concentration chamber comprises an increase in said concentration.

32. A device as in claim 23 wherein said first electrochemical means is disposed on said chamber side of said membrane and said change of concentration of oxygen in said oxygen concentration chamber comprises a decrease in said concentration.

33. A method for the promotion of healing of a wound to or through the skin of a human or animal by controlling the concentration of oxygen at the exposed surface of said wound, which comprises:

forming a device comprising a first chamber distal from said wound, an oxygen chamber open to said wound surface, and fluid communication between said chambers;

disposing ion transport means within said device and between said chambers and in fluid contact with both, said ion transport means comprising a pair of electrodes of opposite polarity with an ion-permeable membrane therebetween, a first electrode of said pair in contact with said first chamber and a second electrode of said pair in contact with said oxygen chamber;

providing an electrical current generator operably connected to said electrodes; and providing an electrically non-conductive adhering member adjacent to said oxygen chamber for adhering said device to a patient's skin surrounding said wound with said oxygen chamber open to said wound;

operating said electrical current generator to cause one of said electrodes to produce an ionic species in the respective chamber, said ionic species to be transported across said ion permeable membrane, and said ionic species to be reacted at said second electrode to be converted to a molecule which results in a net change of concentration of oxygen in said oxygen chamber and adjacent to said exposed surface of said wound.

34. A method as in claim 33 wherein said ionic species comprises a proton or a hydroxyl ion.

35. A method as in claim 33 wherein operation of said electrical current generator results in the electrolytic formation or dissociation of water.

36. A method as in claim 33 further comprising controlling said operation of said generator through air deprivation, an electrical switch, a timer, a sensor responsive to pressure of oxygen in said oxygen concentration chamber or a microprocessor programmed for a plurality of operational sequences or protocols.

37. A method as in claim 33 wherein operation of said electrical current generator produces an increase of concentration of oxygen in said oxygen concentration chamber.

38. A method as in claim 33 wherein operation of said electrical current generator produces a decrease of concentration of oxygen in said oxygen concentration chamber.

39. A method as in claim 33 wherein said first chamber is closably open to ambient air and comprises a closure to close said first chamber to said ambient air, said electrical current generator comprises an air-breathing battery, and said operating comprises closing said closure to deprive said air-breathing battery of air and prevent it from generating electrical current.

40. A method as in claim 33 further comprising simultaneously providing medication to said wound in combination with provision of said oxygen.

41. A method as in claim 33 wherein said medication is in liquid or paste form and is applied topically to said wound prior to said adhering of said device to said patient.

42. A method as in claim 33 wherein said medication is in gaseous or ionized form and is passed through said oxygen chamber to said wound.

43. A method as in claim 33 wherein the following electrolytic reactions occur:

At the anode: $2H_2O \rightarrow 4H^+ + O_2 + 4e^-$

At the cathode: $O_2 + 4H^+ + 4e^- \rightarrow 2H_2O$.

44. A method as in claim 33 wherein the following electrolytic reactions occur:

At the anode: $4OH^- \rightarrow 2H_2O + O_2 + 4e^-$

At the cathode: $O_2 + 2H_2O + 4e^- \rightarrow 4OH^-$.

45. A method as in claim 33 wherein the following electrolytic reactions occur in an acidic medium:

At the anode: $2H_2O \rightarrow O_2 + 4H^- + 4e^-$

At the cathode: $4H^+ + 4e^- \rightarrow 2H_2$.

46. A method as in claim 33 wherein the following electrolytic reactions occur in an alkaline medium:

At the anode: $4OH^- \rightarrow 2H_2O + 4e^- + O_2$

At the cathode: $4H_2O + 4e^- \rightarrow 4OH^- + 2H_2$.

47. A method as in claim 33 wherein the following electrolytic reactions occur in the presence of air:

At the anode: $2H_2O \rightarrow 4H^+ + O_2 + 4e^-$

At the cathode: $O_2(air) + 4H^+ + 4e^- \rightarrow 2H_2O$.

* * * * *